(12) United States Patent
Walter

(10) Patent No.: US 7,650,184 B2
(45) Date of Patent: Jan. 19, 2010

(54) CYLINDRICAL MULTI-CONTACT ELECTRODE LEAD FOR NEURAL STIMULATION AND METHOD OF MAKING SAME

(75) Inventor: Jeryle L. Walter, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 314 days.

(21) Appl. No.: 11/565,547

(22) Filed: Nov. 30, 2006

(65) Prior Publication Data
US 2007/0168004 A1 Jul. 19, 2007

Related U.S. Application Data

(60) Provisional application No. 60/742,161, filed on Dec. 1, 2005.

(51) Int. Cl.
*A61N 1/00* (2006.01)
(52) U.S. Cl. ..................................................... 607/11
(58) Field of Classification Search ................. 607/116, 607/119; 600/372, 374; 604/95, 173, 535, 604/544
See application file for complete search history.

(56) References Cited

U.S. PATENT DOCUMENTS

| | | | | |
|---|---|---|---|---|
| 4,003,382 | A | * 1/1977 | Dyke | 604/103 |
| 4,753,223 | A | * 6/1988 | Bremer | 600/140 |
| 5,040,544 | A | * 8/1991 | Lessar et al. | 607/122 |
| 5,458,629 | A | * 10/1995 | Baudino et al. | 607/116 |
| 5,931,862 | A | 8/1999 | Carson | |
| 6,032,061 | A | * 2/2000 | Koblish | 600/372 |
| 6,421,567 | B1 | * 7/2002 | Witte | 607/122 |
| 6,516,227 | B1 | 2/2003 | Meadows et al. | |
| 6,609,029 | B1 | 8/2003 | Mann et al. | |
| 6,741,892 | B1 | 5/2004 | Meadows et al. | |
| 7,047,082 | B1 | * 5/2006 | Schrom et al. | 607/116 |
| 2005/0070844 | A1 | * 3/2005 | Chow et al. | 604/95.04 |

* cited by examiner

*Primary Examiner*—Angela D Sykes
*Assistant Examiner*—Robert N Wieland
(74) *Attorney, Agent, or Firm*—Darby & Darby P.C.

(57) ABSTRACT

An implantable lead includes a tubular polymer body having a plurality of wire conductors embedded or carried within the inner tube body. A ring contact, e.g., a platinum ring contact, is electrically and mechanically connected to at least one of the plurality of wires at at least one end of the tubular body. In one embodiment, ring contacts are attached at both ends of the tubular body. In another embodiment, a lumen passes longitudinally through the length of the lead body.

19 Claims, 4 Drawing Sheets

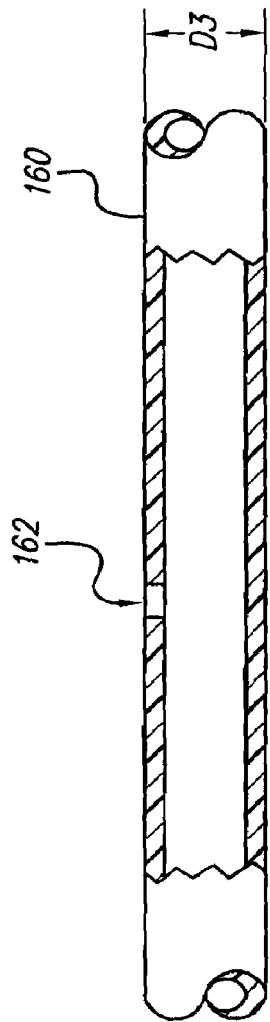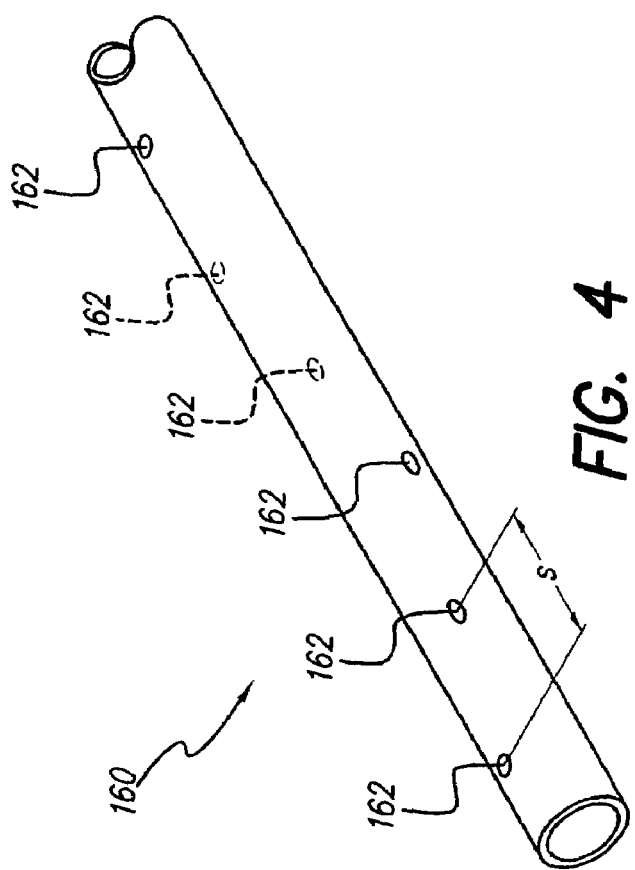
FIG. 3
FIG. 4

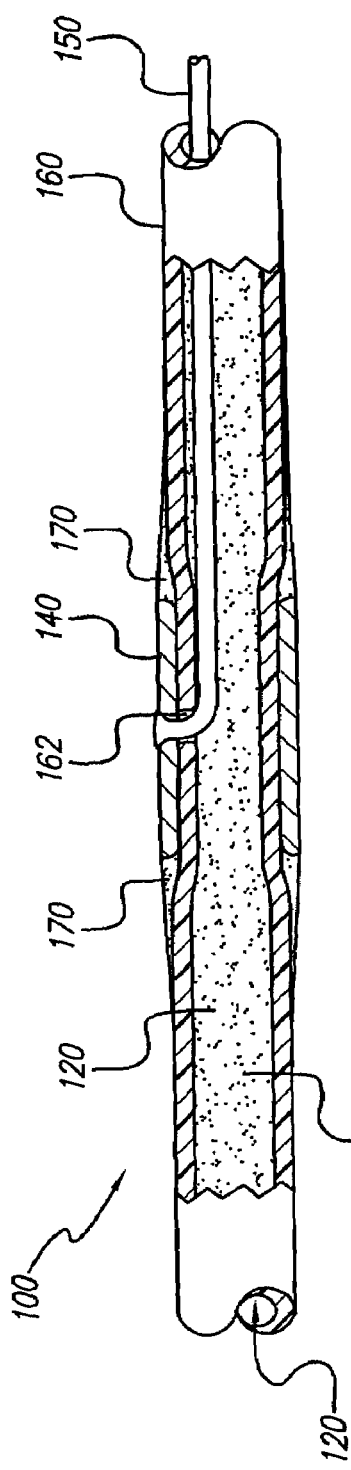
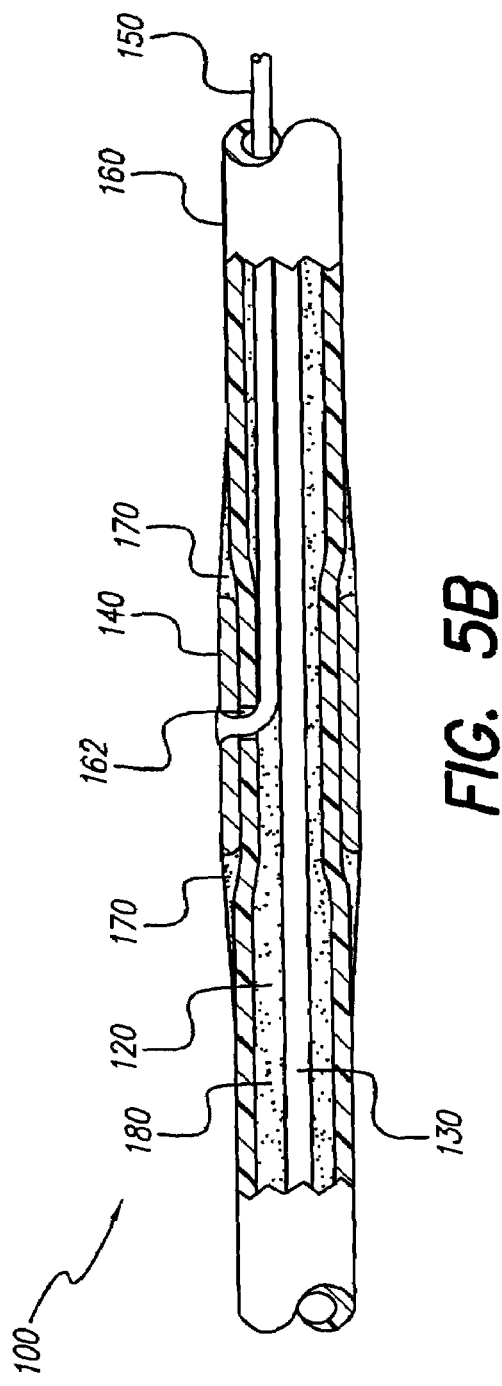
FIG. 5A
FIG. 5B

US 7,650,184 B2

CYLINDRICAL MULTI-CONTACT ELECTRODE LEAD FOR NEURAL STIMULATION AND METHOD OF MAKING SAME

CROSS-REFERENCE TO RELATED APPLICATIONS

This application claims the benefit of U.S. Provisional Application No. 60/742,161, filed Dec. 1, 2005, which application is incorporated by reference in it's entirety.

BACKGROUND OF THE INVENTION

The present disclosure relates to neural stimulation leads, and more particularly to a cylindrical multi-contact electrode lead and method of making such a lead.

The term "lead" will be used herein to describe a plurality of elongate conductors covered by insulation. At a distal end of the lead, each conductor is connected to an exposed (non-insulated) electrode, or electrode contact, which is adapted to provide an electrical interface with the tissue that is to be stimulated. At a proximal end of the lead, each conductor is connected to an exposed terminal, which terminal is adapted to provide an electrical interface with a pulse generator, or with a connector of an extension lead that connects with a pulse generator or other electronic control unit. The pulse generator may be an implantable pulse generator (IPG). The term "electrode array" will refer to that portion of the lead having a plurality of spaced-apart electrode contacts. The terms "electrode" and "electrode array" may be used herein interchangeably.

As the electronic medical devices implanted in patients have become more sophisticated in providing a wider range of stimulation therapies, there has arisen a critical need for an easy-to-manufacture electrode lead that allows the implanted lead system to be reliably connected to an IPG and provide the prescribed therapy. Thus improvements are needed in an easy-to-manufacture, low cost, multi-contact, implantable electrode lead for use in neurostimulation systems.

SUMMARY OF THE INVENTION

The present disclosure is directed to the design and manufacturing technology of a low cost, multi-contact, implantable electrode lead for use in a variety of neurostimulation systems.

Most currently used leads are made with individually insulated wires that are placed loosely within a polymer tubing such as silicone, polyurethane, or polytetrafluoroethylene (PTFE) tubing. A platinum contact is welded at the distal end of each wire, using a controlled spacing in between each contact. Voids between the contacts are then filled with a suitable polymer, such as silicone or polyurethane, using well-known injection molding techniques.

The present disclosure relates to a process of making an implantable multi-contact electrode lead that involves three main steps: (1) attaching wire conductors to platinum ring contacts; (2) making access ports at prescribed locations within a polymer tubing; and (3) assembling the preassembled ring contacts and wire conductors to the polymer tubing. Each of these three main steps may be further broken down into several sub-steps, or operations, as described in more detail below.

BRIEF DESCRIPTION OF THE DRAWINGS

FIG. 3 depicts a second operation associated with making access ports within a polymer tubing;

FIG. 4 shows an embodiment of a polymer tubing having a series of access ports formed in a radial configuration;

FIG. 5A shows a third operation associated with assembling the ring contacts and wire conductors to the polymer tubing;

FIG. 5B shows another embodiment of the same third operation shown in FIG. 5A, adding a central lumen.

Corresponding reference characters indicate corresponding components throughout the several views of the drawings.

DETAILED DESCRIPTION OF THE INVENTION

Figure 1:
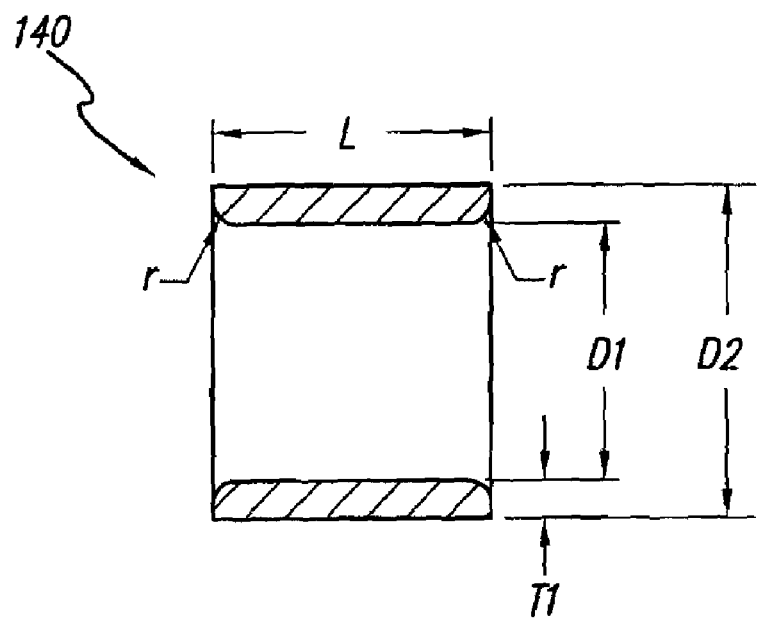
FIG. 1 shows a sectional view of a platinum ring that is used as an electrode contact, prior to attaching such contact to a wire conductor.

The following description is of the best mode presently contemplated for carrying out the invention. This description is not to be taken in a limiting sense, but is made merely for the purpose of describing general principles. The invention is defined in the claims.

The present disclosure is directed to an implantable neural stimulation lead having a multiplicity of electrode contacts at its distal end. A multiplicity of wires, at least one wire for each electrode contact, are embedded or carried within the lead body. At a proximal end of the lead, the wires may be connected to a connector that can be detachably secured to a mating connector of a pulse generator, or other electronic control unit. In some embodiments, the proximal end of the lead, including the wires, may be permanently connected (hard wired) to an electronic control unit, such as an implantable pulse generator (IPG).

The process of making the implantable neural stimulation lead comprises three main steps.

The first step associated with the process of making the implantable neural stimulation lead is attaching wire conductors to ring contacts. The wires may be made from platinum, titanium, stainless steel, or alloys thereof. The ring contacts may be made from platinum, titanium, stainless steel, or alloys thereof.

The second step associated with the process of making the implantable neural stimulation lead is to create access ports to a polymer sheath or tube. The tube may be made from silicone, polyurethane, polytetrafluoroethylene (PTFE), or similar materials. This second main step may come before the above described first main step, or each of these two main steps may be performed simultaneously.

The third step associated with the process of making the implantable neural stimulation lead is to fashion, or to assemble, the ring contacts at a distal end of the lead and to the proximal end of the lead, if needed. Each ring contact is assembled to a distal end or to the proximal end of at the lead using the access ports.

In addition to the three main steps outlined above, there is also a fourth step, at least for some embodiments, but not necessarily part of the present disclosure (and therefore not described in any detail, but known in the lead-making art) of attaching a proximal end of the implantable neural stimulation lead to a connector. Such connector allows the proximal end of the lead to be mechanically and electrically connected to a suitable control unit, such as an implantable pulse generator (IPG), or to a lead extension that connects to an IPG. Alternatively, for some applications, a proximal end of the lead may be directly attached, without the use of a connector, to a suitable control unit, such as an IPG.

Note, for some other applications, the proximal end of the lead may be identical to the distal end of the lead. That is, the proximal end may have lead contacts attached to at least one of the wires passing through the lead body, as is the case at the distal end of the lead. In such instances, the contacts at the proximal end may be welded to the proximal end of the wire conductors, and the resulting lead contacts may be engaged with a suitable connector that forms part of, or is attachable to, an IPG.

The various operations associated with the first three steps of making implantable neural stimulation lead will next be described.

Figure 2:
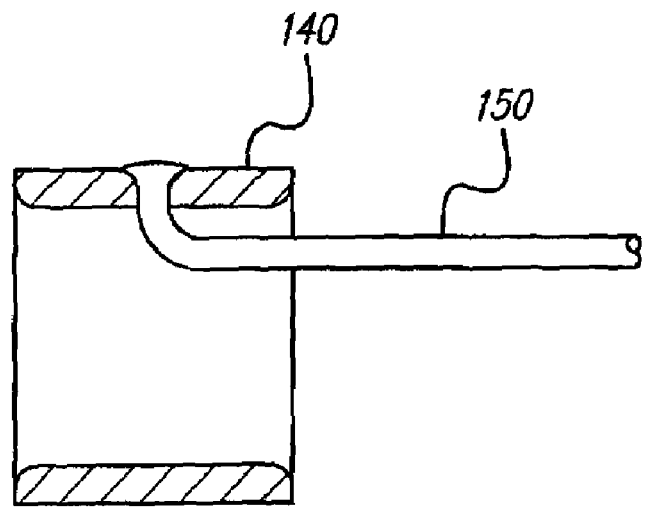
FIG. 2 illustrates a first operation associated with attaching the wire conductors to a ring contacts.

FIG. 1 illustrates a platinum ring contact 140 that may be attached to a distal end of a conductor wire 150 (shown in FIG. 2). Such ring contact 140 may be made using standard manufacturing techniques known in the art. Depending upon the application, and the access port spacing that is used for that application, the ring contact 140 has a length L of from between about 1.0 to 1.5 mm. The thickness T1 of the ring contact 140 is about 0.05 mm. The inside diameter D1 of the ring contacts should be equal to or slightly smaller than the outside diameter D3 of the polymer tubing 160 (shown in FIG. 3). Thus, for one embodiment, where D3 is on the order of 0.8 mm, the inside diameter D1 of the ring contact 140 should be on the order of 0.75 mm. The internal edges of the ring contacts should be rounded, e.g., to have a radius "r", to facilitate sliding of the contacts over the outer surface of tube 160.

For the embodiment shown in FIG. 1, the outside diameter D2 of the ring contact is between about 0.8 mm and 2.0 mm, and may (depending upon the application for which the lead is used) be between about 0.8 mm and 1.2 mm. The inner diameter D1 is between about 0.2 mm and 1.2 mm, and may (depending upon the application) be between about 0.2 mm and 0.4 mm. These dimensions are only exemplary.

Once the ring contacts 140 are formed, then a first operation associated with a first step of making a lead body comprises welding, or otherwise making a secure electrical and mechanical connection, between the lead contact 140 and the conductor wire 150. One end of the conductor wire 150 is welded to the ring contact as shown in FIG. 2. The welding process may consist of using a laser beam. In general, the mechanical construction of joining the wires to the ring contacts is based on well-known techniques used in the art of making leads. As seen in FIG. 2, the length of the wire conductor 150 is extended along an opening of the ring contact 140. The welding operation illustrated in FIG. 2 is performed on all contacts.

Next, a second step associated with the process of making the implantable neural stimulation lead is commenced. This second step, as indicated previously, comprises fashioning, or creating access holes 162 to the polymer tubing 160. Each access hole 162 or "port" can be pre-cut in a radial configuration as shown in FIG. 4. Other hole patterns may also be used, e.g., linear or random hole patterns. Such access holes 162 are made using a suitable stamping tool having a sharp tip configured to stamp a hole and remove the excess material. Such process may be accomplished relatively easily using a holding fixture equipped with a pressing punch. A suitable number of access ports are created for each ring contact, e.g., from 1 to 4. The desired access hole spacing S is determined by the distance L of the ring contacts plus a distance of about between 0.5 mm to 2.0 mm (the desired gap between each ring contact). For some applications, a ring contact 140 may be desired on both ends of the polymer body 160, i.e., on a distal end and on a proximal end, thus a suitable number of access ports may be created on both ends of the polymer body 160. (The ring contacts on the proximal end, if used, can then interface with a suitable connector into which the proximal end of the lead may be detachably secured.) As stated above, this second step may come before the above described first step, or each of these two main steps may be performed simultaneously.

Next, a third step associated with the process of making the implantable neural stimulation lead is commenced. This third step, as indicated previously, comprises fashioning, or assembling, and connecting lead contacts to a distal end of the lead. Like the first step, this third step is also broken down into several operations.

As shown in FIG. 5A, the several operations consist of (a) threading the wire conductor 150 through an access hole 162, starting from the furthest hole from the distal end of the polymer tubing; (b) adding tension to the polymer tubing 160 to allow the ring contact 140 to easily slide over the tubing 160; (c) positioning each ring contact 140 over the access hole 162; (d) repeating steps a-c for each ring contact (e) adding an adhesive material 170, such as implantable medical grade epoxy, to fill the area around each ring contact 140. Voids between the contacts are then filled with a suitable polymer, such as silicone or polyurethane, for example filler material 180 may be added to the inside area 120 to provide stiffness to the polymer tubing using well-known injection molding techniques. If a longitudinal lumen is desired as shown in FIG. 5B, a spacer may be inserted through the inside area 120 before the filler material 180 is added and thus, when the spacer is removed, a central longitudinal lumen 130 is formed through the entire length of the lead body 100.

Figure 6:
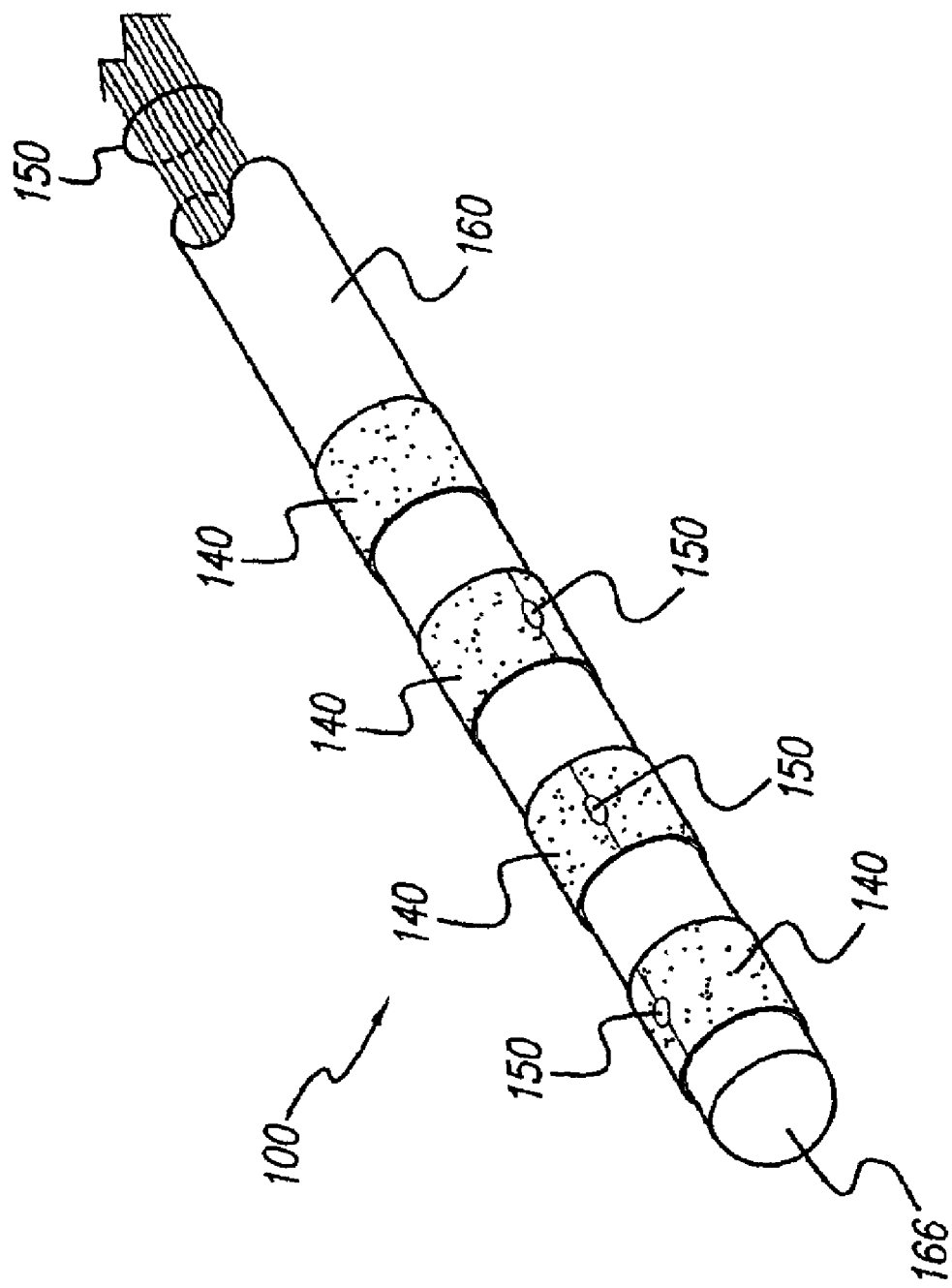
FIG. 6 shows an embodiment of the distal end of a cylindrical multi-contact electrode lead assembly.

The result of the third operation shown in FIG. 6, consists of multiple wires 150 being embedded or carried inside the tubular polyurethane tubing 160. The desired contact ring spacing is determined by the spacing S of the pre-cut access holes 162.

Another operation associated with the third step comprises inspecting the lead body 100 and cutting it to a desired length.

Once the inspection operation has been performed, then a final operation involves trimming and sealing the end of the lead where the contacts are attached. If contacts 140 are attached to both the proximal and distal ends of the body 100, then trimming and perhaps sealing should be done at both ends of the lead body. (Sealing may only be needed at the distal end 166 of the lead body 100, if a thin stylet is to be inserted in the lumen during placement of the lead.) If the lead contacts 140 are attached to only the distal end of the lead body, then whatever connection needs to take place at the proximal end can take place, e.g., directly connecting the proximal end of the lead 100 to an IPG.

While the invention herein disclosed has been described by means of specific embodiments and applications thereof, numerous modifications and variations could be made thereto by those skilled in the art without departing from the scope of the invention set forth in the claims.

What is claimed is:

1. A method of making an implantable lead comprising:
providing a plurality of ring contacts, wherein each ring contact is mechanically and electrically connected to at least one of a plurality of wire conductors;
creating a plurality of access ports in at least a distal end of a polymer tube body, wherein the access ports extend from an exterior of the polymer tube body to an inside area of the polymer tube body;
threading each wire conductor through a corresponding one of the access ports;
sliding the ring contacts over the tube body; and
attaching the plurality of ring contacts to at least a distal end of the tube body with an adhesive;
wherein threading each wire conductor through a corresponding one of the access ports and sliding the ring contacts over the tube body occur after providing a plurality of ring contacts mechanically and electrically connected to at least one of a plurality of wire conductors,
wherein the adhesive is applied to at least one edge of the ring contact after the ring contacts are slid over the tube body, and
wherein the adhesive at least partially fills a deformation created by constriction of the tubular body by the ring contact.

2. The method of claim 1 further including adding a filler material to the inside area of the polymer tube body after the wire conductors are threaded through the access ports.

3. The method of claim 1 wherein attaching the plurality of ring contacts comprises adding a medical grade epoxy.

4. The method of claim 1 wherein providing a plurality of ring contacts comprises laser welding each ring contact to at least one of the plurality of wire conductors.

5. The method of claim 1 wherein the polymer tube body comprises silicone, polyurethane, or polytetrafluoroethylene (PTFE).

6. The method of claim 1, wherein creating a plurality of access ports comprises creating the access ports spaced apart a distance S.

7. The method of claim 1, wherein creating a plurality of access ports comprises forming the access ports using a stamping tool having a sharp tip configured to stamp a hole and remove the excess tube body material.

8. A method of making an implantable lead comprising:
providing a plurality of ring contacts, wherein each ring contact is mechanically and electrically connected to at least one of a plurality of wire conductors;
creating a plurality of access ports in at least a distal end of a polymer tube body, wherein the access ports extend from an exterior of the polymer tube body to an inside area of the polymer tube body;
threading each wire conductor through a corresponding one of the access ports;
sliding the ring contacts over the tube body; and
inserting a spacer into the inside area of the polymer tube body before adding a filler material to the inside area and then removing the spacer, thereby forming a central lumen within the polymer body,
wherein threading each wire conductor through a corresponding one of the access ports and sliding the ring contacts over the tube body occur after providing a plurality of ring contacts mechanically and electrically connected to at least one of a plurality of wire conductors.

9. A method of making an implantable lead comprising:
providing a plurality of ring contacts, wherein each ring contact is mechanically and electrically connected to at least one of a plurality of wire conductors;
creating a plurality of access ports in at least a distal end of a polymer tube body, wherein the access ports extend from an exterior of the polymer tube body to an inside area of the polymer tube body;
threading each wire conductor through a corresponding one of the access ports; and
sliding the ring contacts over the tube body,
wherein threading each wire conductor through a corresponding one of the access ports and sliding the ring contacts over the tube body occur after providing a plurality of ring contacts mechanically and electrically connected to at least one of a plurality of wire conductors, and
wherein sliding the ring contact over the tube body comprises applying tension to the tube body to allow each of the ring contacts to slide over the corresponding one of the access ports.

10. An implantable lead comprising:
a tubular body having a plurality of wire conductors disposed within the tubular body, wherein each wire conductor is threaded through an access port in the tubular body;
a plurality of ring contacts, wherein each ring contact is electrically and mechanically attached to at least one of the plurality of wire conductors at least one end of the tubular body; and
an adhesive disposed on at least one edge of at least one ring contact, wherein the adhesive at least partially fills a deformation created by constriction of the tubular body by the ring contact.

11. The implantable lead of claim 10 wherein the plurality of ring contacts are mechanically and electrically attached to the plurality of wire conductors at both ends of the tubular body.

12. The implantable lead of claim 10 wherein the tubular body is made from silicone, polyurethane, or polytetrafluoroethylene (PTFE).

13. The implantable lead of claim 10 wherein the conductor wires are made from platinum, titanium, stainless steel or alloys thereof.

14. The implantable lead of claim 10 wherein an internal edge of the ring contact is rounded.

15. An implantable neural stimulation system, comprising:
an electronic control unit; and
an implantable lead electrically coupled to the electronic control unit, the implantable lead comprising
a tubular body having a plurality of access ports formed therethrough,
a plurality of ring contacts disposed on the tubular body,
a plurality of wire conductors, wherein each of the wire conductors is electrically and mechanically attached to a corresponding one of the ring contacts and is threaded through a corresponding one of the access ports over which the corresponding one of the ring contacts is disposed; and
an adhesive disposed on at least one edge of at least one ring contact, wherein the adhesive at least partially fills a deformation created by constriction of the tubular body by the ring contact.

16. The implantable neural stimulation system of claim 15, wherein the electronic control unit comprises an implantable pulse generator.

17. The implantable neural stimulation system of claim 15, wherein the access ports are staggered radially around the tubular body.

18. The implantable neural stimulation system of claim 15, wherein the ring contacts are disposed at a distal end of the lead.

19. The implantable neural stimulation system of claim 15, wherein the ring contacts are disposed at both a distal end of the lead and at a proximal end of the lead.

* * * * *

UNITED STATES PATENT AND TRADEMARK OFFICE
CERTIFICATE OF CORRECTION

PATENT NO. : 7,650,184 B2
APPLICATION NO. : 11/565547
DATED : January 19, 2010
INVENTOR(S) : Jeryle L. Walter It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 364 days.

Signed and Sealed this

Twenty-third Day of November, 2010

David J. Kappos
*Director of the United States Patent and Trademark Office*